US00PP28989P3

(12) United States Plant Patent
Kordes

(10) Patent No.: US PP28,989 P3
(45) Date of Patent: Feb. 27, 2018

(54) MINIATURE ROSE PLANT NAMED 'KORPOT060'

(50) Latin Name: *Rosa hybrida*
Varietal Denomination: KORpot060

(71) Applicant: W. Kordes Söhne Rosenschulen GmbH & Co. KG, Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Offenseth-Sparrieshoop (DE)

( * ) Notice: Subject to any disclaimer, the term of this patent is extended or adjusted under 35 U.S.C. 154(b) by 23 days.

(21) Appl. No.: 14/998,642

(22) Filed: Jan. 25, 2016

(65) Prior Publication Data

US 2017/0215311 P1 Jul. 27, 2017

(51) Int. Cl.
*A01H 5/02* (2006.01)

(52) U.S. Cl.
USPC ..... Plt./121

(58) Field of Classification Search
USPC ..... Plt./121
See application file for complete search history.

*Primary Examiner* — Keith O Robinson
(74) *Attorney, Agent, or Firm* — Samuel R. McCoy, Jr.

(57) ABSTRACT

'KORpot060' is a new and distinct variety of *Rosa hybrida* which is characterized by the combination of a compact growth habit, dark green and glossy foliage, good resistance to downy mildew and powdery mildew, white very-double flowers with deep pink petal margins, and very good shelf life as a pot plant. The new variety propagates successfully by stem cuttings and has shown to be uniform and stable in the resulting generations from asexual propagation.

1 Drawing Sheet

Latin name of genus and species: The Latin name of the genus and species of the novel variety disclosed herein is *Rosa hybrida*.

Variety denomination: The inventive variety of *Rosa hybrida* disclosed herein has been given the variety denomination 'KORpot060'.

BACKGROUND OF THE INVENTION

Parentage: The *Rosa hybrida* variety 'KORpot060' is the result of a controlled cross-pollination breeding program carried out by the inventor in Offenseth-Sparrieshoop, Germany. The objective of the said breeding program was to create a new and distinct rose plant with unique qualities, such as:

1. Uniform growth and flowering;
2. Abundant attractive, pink colored recurrent flowers;
3. Attractive and abundant foliage; and
4. Excellent shelf life for the plant when grown as a commercial pot rose.

This combination of qualities is not present in prior rose cultivars known to the inventor. These objectives have been substantially achieved and in that distinguish 'KORpot060' from all other varieties known to the inventor.

'KORpot060' is a seedling selection which resulted from the controlled pollination of *Rosa hybrida* 'KORsalexa' (not patented), the seed parent, and *Rosa hybrida* 'KORpot012' (not patented), the pollen parent, both developed and owned by the same inventor, during the summer of 2011. As part of a rose development program, Tim-Hermann Kordes germinated seeds from the aforementioned hybridization during the following winter and conducted evaluations and observations on the resulting seedlings in a controlled environment in Offenseth-Sparrieshoop, Germany. The resulting seedlings exhibited distinctive physical and biological characteristics. The new rose plant was selected as a single plant in April of 2012 from the seedling beds due to its superior characteristics and asexually propagated for further evaluation. This new and distinctive rose variety was given the name 'KORpot060'.

Asexual Reproduction: The first asexual propagation of 'KORpot060' was performed in July of 2012 at the inventor's nursery in Offenseth-Sparrieshoop, Germany. Subsequently, 'KORpot060' has been successfully propagated by stem cuttings and in Jackson County, Oreg. These initial and other subsequent propagations conducted in controlled environments demonstrate that 'KORpot060' reproduces true to type in successive generations of asexual reproduction.

SUMMARY OF THE INVENTION

The following characteristics have been repeatedly observed and represent the distinguishing characteristics of the new *Rosa hybrida* cultivar 'KORpot060'. These traits, in combination, distinguish 'KORpot060' as a new and distinct cultivar.

1. *Rosa hybrida* 'KORpot060' exhibits a compact growth habit; and
2. *Rosa hybrida* 'KORpot060' exhibits dark green and very glossy foliage; and
3. *Rosa hybrida* 'KORpot060' exhibits good resistance to downy mildew and powdery mildew; and
4. *Rosa hybrida* 'KORpot060' exhibits a very double petal count; and
5. *Rosa hybrida* 'KORpot060' exhibits a small to medium flower size for a miniature rose; and
6. *Rosa hybrida* 'KORpot060' exhibits very good shelf life as a pot plant; and 7. *Rosa hybrida* 'KORpot060' exhibits a white flower color with deep pink margins, at anthesis.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpot060', taken from twelve month old plants.

DETAILED BOTANICAL DESCRIPTION

The following is a detailed botanical description of a new and distinct variety of *Rosa hybrida* known as 'KORpot060', based upon field observations made in July of 2015, from twelve month old container-grown plants in a greenhouse environment in Jackson County, Oreg. Those skilled in the art will appreciate that certain characteristics will vary with older or, conversely, with younger plants. 'KORpot060' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2001 edition except where common terms of color are used.

A botanical description of 'KORpot060' and comparisons with other varieties of *Rosa hybrida* are provided below.

General plant description:

*Growth rate*.—Moderately vigorous.

*Growth habit*.—Compact.

*Mature dimensions*.—24 cm tall and 20 cm wide, on average, when grown as a 15 cm nursery pot.

*Cold hardiness*.—Unknown.

*Propagation*.—Stem cuttings.

*Disease resistance*.—Good resistance to powdery mildew (*Sphaerotheca pannosa*) and downy mildew (*Peronospora sparsa*) in a greenhouse environment in Jackson County, Oreg.

Root system: Fibrous.

Stems:

*Stem color*.—Young stems are Yellow-Green Group 144A; mature stems are Yellow-Green Group 146A.

*Anthocyanin intonations*.—Greyed-Red Group 181A intonations are present on new growth.

*Stem surface texture*.—Both immature and mature stems exhibit a smooth texture.

*Stem dimensions*.—Typical mature stems are approximately 20 to 25 cm long and 4 mm in diameter.

*Prickles*.—Incidence — Present; 8 prickles per 10 cm of stem, on average. Size — Average length is 2 to 4 mm. Immature prickle color — Yellow-Green Group 145B. Mature prickle color — Yellow-Green Group 145B and senescing to Greyed-Orange Group 177C. Anthocyanin intonations — None present. Shape — Linear. Texture — Smooth.

Leaves:

*Arrangement*.—Imparipinnate compound leaves; mature axillary leaves consisting of 5 leaflets.

*Attachment*.—Petiolate.

*Dimensions*.—60 to 65 mm long and 40 to 45 mm wide, on average.

*Abundance*.—Above average; 60 to 65 leaves per plant.

*Stipules*.—Size — 7 mm long and 3 to 4 mm wide. Stipule color — Yellow-Green Group 146A, and 146C on the midrib. Anthocyanin intonations — None. Stipitate glands — Abundant on the margins. Margins — Glandular toothed. Texture, adaxial surfaces — Smooth with fine hairs. Texture, abaxial surfaces — Glabrous. Apex — Apiculate. Base — Winged.

*Petiole*.—Length — Average 12 mm. Diameter — Average 1 mm. Petiole color, adaxial and abaxial surfaces — Yellow-Green Group 146A. Margins — Entire with occasional stipitate glands. Anthocyanin intonations — None. Prickles — One prickle present on the abaxial surface of the petiole. Stipitate glands — Limited number; present on the margins. Texture — Smooth, with a few fine white hairs, White Group 155C, on the adaxial surface. Strength — Somewhat strong.

*Rachis*.—Length — Average 10 to 14 mm. Diameter — Average 1 mm. Color — Yellow-Green Group 146B. Anthocyanin intonations — None present. Margins — Entire with occasional stipitate glands. Prickles — A few small prickles underneath. Stipitate glands — Limited; present along margins and underneath. Texture — Papillate.

*Leaflets*.—Quantity — Normally 5 leaflets on normal leaves in middle of the stem. Dimensions — Average size of the terminal leaflet is 25 mm long and 15 mm wide. Shape — Ovate. Apex — Acuminate. Base — Obtuse. Margins — Serrated; no undulation. Luster and texture, adaxial surface — Semi-glossy and smooth. Luster and texture, abaxial surface — Matte and rugose. Juvenile foliage color, adaxial surface — Yellow-Green Group 146A. Juvenile foliage color, abaxial surface — Yellow-Green Group 146B. Mature foliage color, adaxial surface — Yellow-Green Group 147A. Mature foliage color, abaxial surface — Yellow-Green Group 147B. Anthocyanin intonations — Greyed-Red Group 182A. Intonations are predominantly present on abaxial surface and margins of juvenile leaflets. Venation — Reticulate. Petiolule — Dimensions — 1.5 mm long and 1 mm in diameter. Petiolule color, adaxial surface — Yellow-Green Group 145A. Petiolule color, abaxial surface — Yellow-Green Group 145A. Prickles — None present. Texture, adaxial and abaxial surfaces — Smooth. Margins — Entire with occasional stipitate glands.

Inflorescence:

*Inflorescence type*.—Determinate. Most commonly, solitary to simple corymb of 2 to 3 flowers on apical and flowering lateral shoots.

*Blooming habit*.—Recurrent.

*Quantity of flowers*.—Solitary to up to 3 flower buds per inflorescence.

*Size*.—75 mm tall and 50 mm wide, on average.

*Peduncle*.—Length — 10 to 30 mm average length. Diameter — 2 to 3 mm average diameter. Color — Yellow-Green Group 146A. Anthocyanin intonations — None. Strength — Strong. Texture and pubescence — Smooth; glabrous.

Flowering laterals: None present.

Bud:

*Bud form*.—Short; globular.

*Size*.—Upon opening, 20 to 25 mm in length from base of receptacle to distal end of bud and 14 to 17 mm diameter at its widest point.

*Texture*.—Smooth.

*Color, as sepals first unfold*.—Orange Group 27B, with intonations of Red-Purple Group N57B on petal margins.

*Color when one-quarter open, inner side*.—Marginal zone — Green-Yellow Group 1D, with intonations of Red-Purple Group N57B. Middle zone — Green-Yellow Group 1D. Basal zone — Green-Yellow Group 1C.

*Color when one-quarter open, outer side*.—Marginal zone — Green-Yellow Group 1D, with intonations of Red-Purple Group N57B. Middle zone — Green-Yellow Group 1C. Basal zone — Green-Yellow Group 1C.

Flower:

*Pedicel*.—Surface — Limited number of stipitate glands are present. Length — 15 to 25 mm, on average. Diameter — 2 to 3 mm, on average. Color — Yellow-Green Group 144A. Anthocyanin intonations — Not present. Strength — Somewhat strong. Texture — Papillate.

*Calyx*.—General — Comprised of five polysepalous sepals, with weak to moderate foliaceous appendages present on three of the five sepals. Diameter of calyx — 40 to 50 mm, at anthesis. Sepals — Color, adaxial surface — A combination of both Yellow-Green Group 144A and Green Group 137A. Color, abaxial surface — A combination of Yellow-Green Group 147B and 147C. Anthocyanin intonations — Not present. Size — 18 to 24 mm long and 5 to 6 mm wide, on average. Apex — Both cirrose and apiculate apices observed. Base — Flat at union with receptacle. Quantity — Five. Texture, adaxial surface — Hoary. Texture, abaxial surface — Smooth with a few fine white hairs, White Group 155C. Margins — Both glandular toothed and ciliate margins observed. Stipitate glands — Limited number on the abaxial surface and along margins.

*Corolla*.—General shape of corolla — Round to star-shaped. Shape of corolla when viewed from the side — Upon opening, upper portion — Flattened convex. Upon opening, lower portion — Flattened convex. Open flower, upper portion — Flattened convex. Open flower, lower portion — Concave. Dimensions — Medium for a miniature rose. When open, the average flower diameter is 40 mm and the average flower height is 15 to 20 mm. Fragrance — Light. Duration — On the plant 18 to 24 days. Senesced petals clinging. Petals — Petal count — Exhibits very double flowers with approximately 90 petals under normal conditions. Petal arrangement — Formal. Petal reflex — Doubly reflexed. Timing of petal reflex — One-by-one; outermost petals reflexing first. Petal margin — Entire. Petal shape — Outermost petals are elliptical; innermost petals are cuneate. Apex — Acuminate. Base — Outermost petals are obtuse; innermost petals are cuneate. Dimensions — 10 to 18 mm long and 5 to 15 mm wide. Texture, inner surface — Smooth. Texture, outer surface — Smooth. Petal color, upon opening — Outermost petals, inner and outer surfaces — Marginal zone — Yellow-Green Group 150D, with intonations of Red-Purple Group N57A at the margins. Middle zone — Yellow-Green Group 150D. Basal zone — Green-Yellow Group 1C. Innermost petals, inner and outer surfaces — Marginal zone — Green-Yellow Group 1C, with intonations of Red-Purple Group N57A at the margins. Middle zone — Green-Yellow Group 1C. Basal zone — Green-Yellow Group 1B. Basal petal spots, upon opening — No distinct coloration at the petal base. Petal color, after opening — Outermost petals, inner and outer surfaces — Marginal zone — Yellow-Green Group 150D, with intonations of Red-Purple Group N57A at the margins. Middle zone — Yellow-Green Group 150D. Basal zone — Yellow-Green Group 150D. Innermost petals, inner and outer surfaces — Marginal zone — Yellow Group 3C, with intonations of Red-Purple Group N57A at the margins. Middle zone — Yellow Group 3C. Basal zone — Yellow Group 3C. Basal petal spots, after opening — No distinct coloration at the petal base. General Tonality — Yellow Group 2D, with intonations of Red-Purple Group N57B, fading to Red-Purple 58D. Petaloids — Quantity — 15 petaloids per flower, on average. Dimensions — Approximately 5 to 9 mm long and 2 to 4 mm wide. Color, inner and outer surfaces — Marginal zone — Yellow Group 1C, with intonations of Red-Purple Group N57A at the margins. Middle zone — Yellow Group 1C. Basal zone — Yellow Group 1A. Margins — Undulated. Shape — Some irregularity; generally spatulate to oblanceolate. Apex — Acuminate. Base — Both cuneate and attenuate observed. Texture, inner and outer surfaces — Smooth.

Reproductive organs:

*Stamens*.—Quantity — Approximately 35, on average, and regularly arranged around the styles. Anthers — Shape — Reniform. Dimensions — 1.5 mm long and 1 mm wide, on average. Color — Yellow-Orange Group 18A. Pollen — Generally absent. Filaments — Color — Green-White Group 157B. Length — 3 mm.

*Pistils*.—Quantity — Average; approximately 60. Stigmas — Dimensions — 0.5 mm long and 0.5 mm wide. Location — Equal in position to anthers. Color — Green-White Group 158A. Styles — Length — Approximately 4 mm long. Color — Yellow-Green Group 145D, with intonations of Red-Purple Group N57A.

*Ovary*.—Dimensions — 2 mm long and 1 mm in diameter. Color — Yellow-Green Group 145C.

*Receptacle*.—Shape — Funnel-shaped. Dimensions — Approximately 5 mm high and 7 mm wide. Surface — Glaucous and lightly pubescent; limited number of fine white hairs, White Group 155C. Color — Yellow-Green Group 144B.

Hips and seed formation: Not observed.

Comparisons With the Parents

The new rose plant may be distinguished from its seed parent, 'KORsalexa', by the following combination of characteristics:

1. 'KORpot060' exhibits a compact growth habit, whereas 'KORsalexa' exhibits a tall, upright growth habit.

2. 'KORpot060' exhibits a short, globular flower bud, whereas 'KORsalexa' exhibits a long, pointed ovoid bud form.
3. The flowers of 'KORpot060' have approximately 90 petals whereas, the flowers of 'KORsalexa' have approximately 55 to 65 petals.

The new rose plant may be distinguished from its pollen parent, 'KORpot012', by the following combination of characteristics:

1. 'KORpot060' exhibits a generally symmetric plant shape, whereas 'KORpot012' exhibits a partially asymmetric plant shape.
2. 'KORpot060' exhibits a white flower with deep pink margins, whereas 'KORpot012' exhibits a white flower with soft pink margins.
3. The flowers of 'KORpot060' exhibits very good shelf life as a pot plant, whereas the shelf life of 'KORpot012' as a pot plant is not as good.

Comparison With the Most Similar *Rosa* Cultivar Known to the Inventor

For a comparison, several physical characteristics of the rose variety 'KORpot001', a rose variety from the same inventor described and illustrated in U.S. Plant Pat. No. 23,954 are compared to 'KORpot060' in Chart 1.

CHART 1

| Characteristic | 'KORpot060' | 'KORpot001' |
|---|---|---|
| General tonality of the flower. | Yellow Group 2D with intonations of Red Purple 58D. | Yellow-Orange Group 20C. |
| Pistil count. | 60. | 25 to 30. |
| Flower petal count. | 90. | 70 to 85. |

That which is claimed is:

1. A new and distinct variety of rose plant named 'KORpot060', as described and illustrated herein.

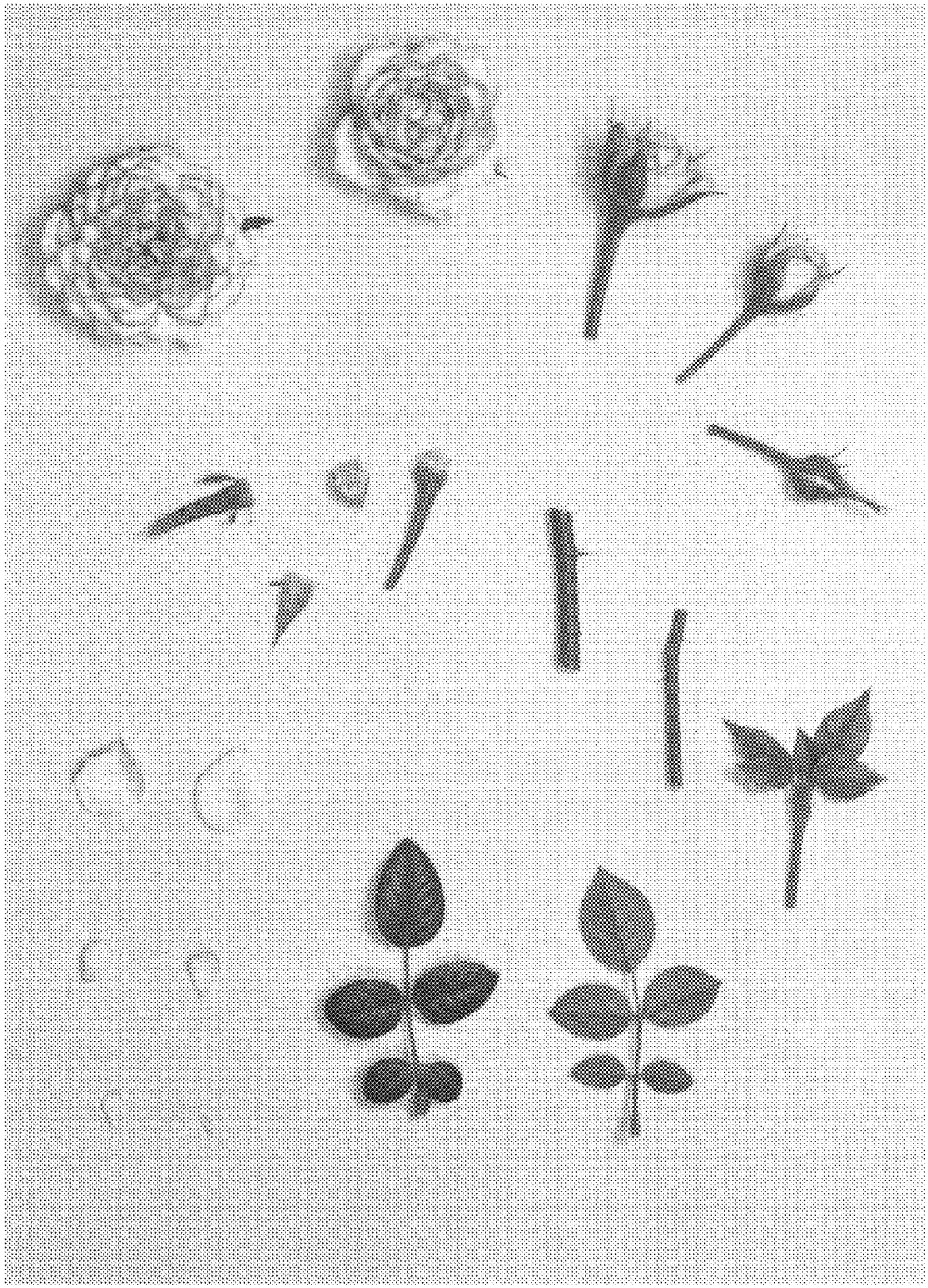

* * * * *